US00PP30737P3

(12) United States Plant Patent
Kromm

(10) Patent No.: US PP30,737 P3
(45) Date of Patent: Jul. 23, 2019

(54) ***TILIA* TREE NAMED 'KROMM'**

(50) Latin Name: *Tilia americana*
Varietal Denomination: KROMM

(71) Applicant: Darrell Kromm, Reeseville, WI (US)

(72) Inventor: Darrell Kromm, Reeseville, WI (US)

( * ) Notice: Subject to any disclaimer, the term of this patent is extended or adjusted under 35 U.S.C. 154(b) by 0 days.

(21) Appl. No.: 15/732,650

(22) Filed: Dec. 7, 2017

(65) Prior Publication Data

US 2019/0183000 P1 Jun. 13, 2019

(51) Int. Cl.
*A01H 5/00* (2018.01)

(52) U.S. Cl.
USPC ..... Plt./222

(58) Field of Classification Search
USPC ..... Plt./222
CPC ... A01H 5/00; A01H 5/02; A01H 6/60; A01H 6/00
See application file for complete search history.

*Primary Examiner* — June Hwu
(74) *Attorney, Agent, or Firm* — Cassandra Bright

(57) ABSTRACT

A new and distinct *Tilia americana* tree named 'KROMM' is disclosed, characterized by a unique narrow pyramidal shape and a dense, compact morphology. Foliage is a lustrous dark green, with this attractive quality maintained late into the season. During early Fall foliage of the new variety is still attractive when many *Tilia americana* trees have a dull, withering appearance. The new variety is an ornamental tree, useful for landscape purposes.

4 Drawing Sheets

Latin name of the genus and species: *Tilia americana.*
Variety denomination: 'KROMM'.

BACKGROUND OF THE INVENTION

The new cultivar is a product of chance discovery. The new variety was discovered as a chance seedling emerging among an outdoor field planting of several cultivars of *Tilia americana* trees. The inventor discovered this seedling in 1985 at a commercial nursery in Reeseville, Wis. The inventor observed the chance seedling for some years, making a selection of this new tree in 1991.

Asexual reproduction of the new cultivar 'KROMM' was first performed during 1993 at a commercial nursery in Reeseville, Wis. This was conducted by the conventional commercial practice of a chip bud graft onto *Tilia americana* seedling rootstock. Subsequent propagation of three generations has shown that the unique features of this cultivar are stable and have been reproduced true to type in successive generations.

SUMMARY OF THE INVENTION

The cultivar 'KROMM' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'KROMM' grown in Reeseville, Wis. These characteristics in combination distinguish 'KROMM' as a new and distinct *Tilia americana* cultivar:

1. Pyramidal shaped tree with an overall more narrow shape.
2. Very dense, branching, forming more compact morphology.

3. Lustrous dark green foliage character is maintained late into season.
4. Attractive foliage in September when many *Tilia americana* have a dull, withering appearance.

PARENT COMPARISON

The breeder cannot confirm parent varieties, as several *Tilia americana* varieties were present in the planting in which the new variety was discovered.

COMMERCIAL COMPARISON

Plants of the new cultivar 'KROMM' are similar to plants of *Tilia americana* 'Redmond', unpatented, in most horticultural characteristics, however, plants of the new cultivar 'KROMM' differ in the following;

1. The new variety produces branches at a more acute angle than 'Redmond'.
2. Trees of the new variety have a narrower overall crown size than 'Redmond'.
3. Trees of 'KROMM' have denser branching than trees of 'Redmond'.
4. Trees of 'KROMM' have foliage which maintains a dark color and luster during early Fall, whereas foliage of 'Redmond' has lost luster and begin fading color in September.

Plants of the new cultivar 'KROMM' are similar to plants of the unpatented commercial variety, *Tilia americana* 'McKSentry' in most horticultural characteristics, however, plants of the new cultivar 'KROMM' differ in the following;

1. The new variety produces branches at a more acute angle than 'McKSentry'.
2. Trees of the new variety have a narrower overall crown size than 'McKSentry'.

3. Trees of 'KROMM' have denser branching than trees of 'McKSentry'.

BRIEF DESCRIPTION OF THE PHOTOGRAPHS

The accompanying photograph in FIG. 1 illustrates in full color a typical tree of 'KROMM' in Reeseville, Wis., during early Fall. Age of the tree in FIG. 1 is approximately 10 to 11 years.

Figure 1:
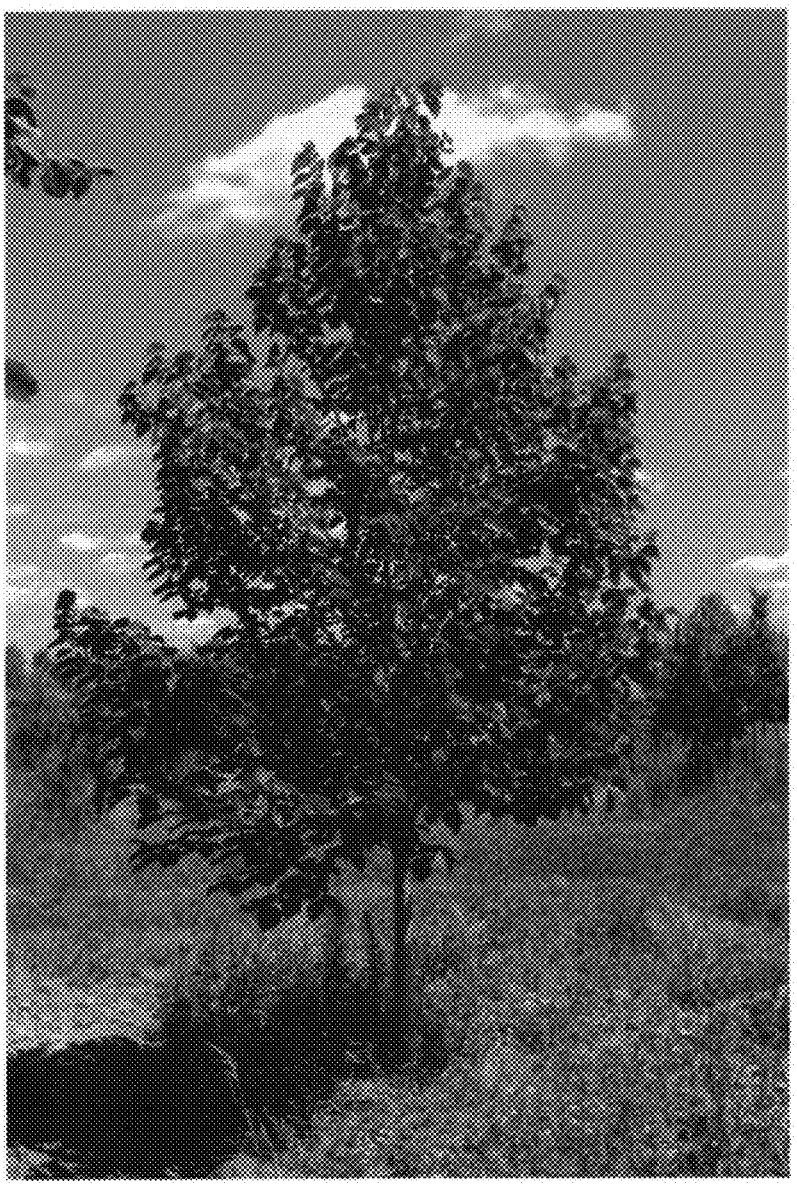
Figure 2:
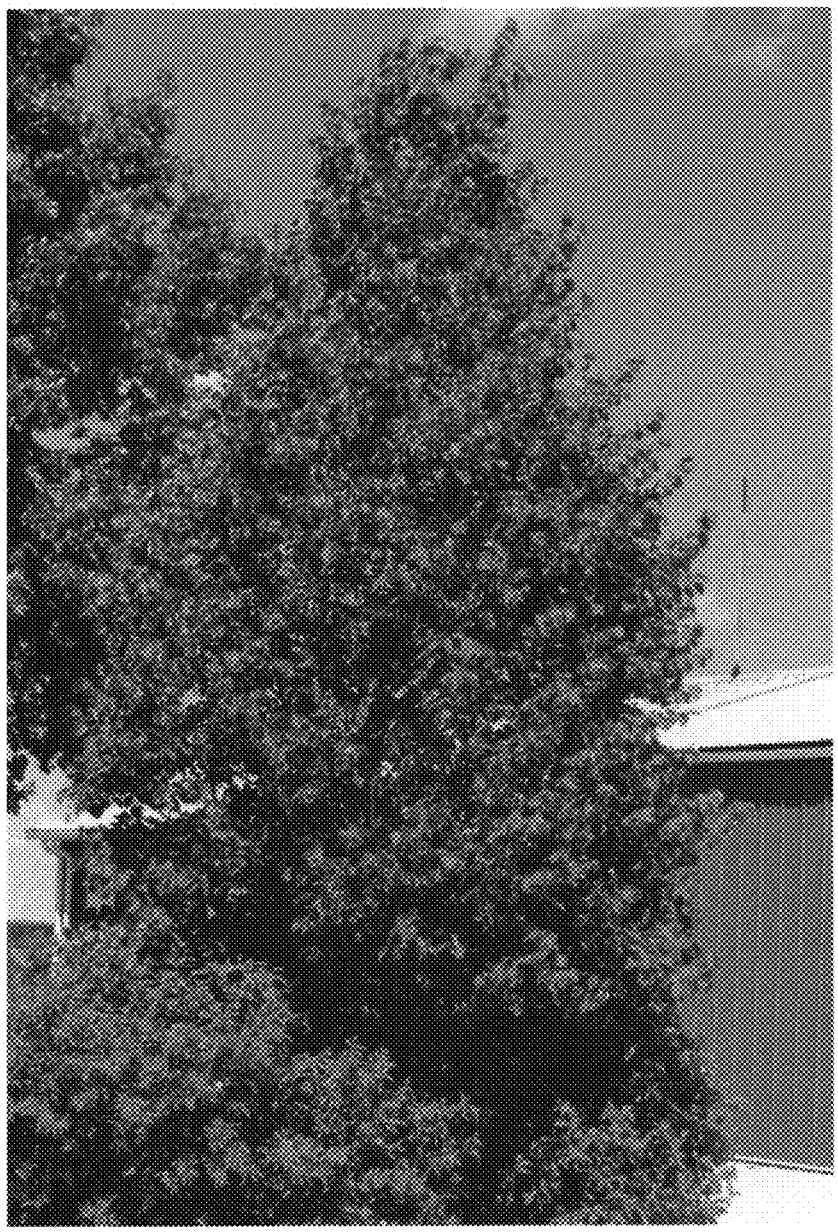
FIG. 2 illustrates a tree of 'KROMM' at approximately 14 years.
Figure 3:
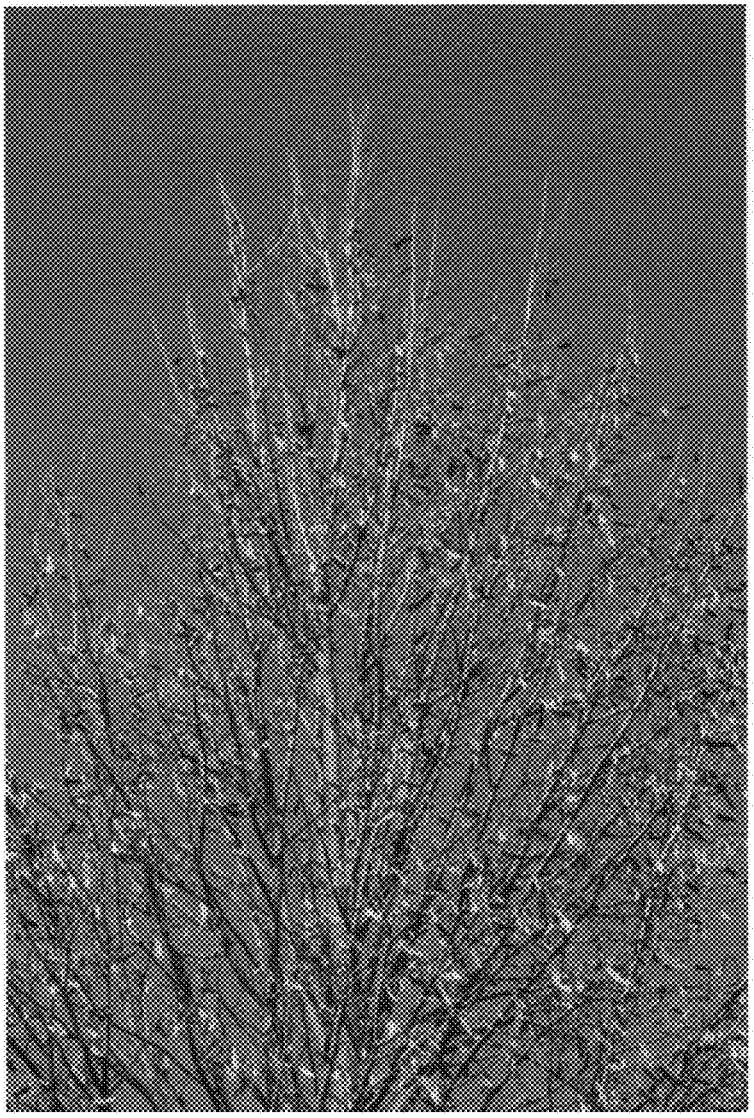
FIG. 3 illustrates a view of the crown of a tree of 'KROMM', with typical dense and acute branching.
Figure 4:
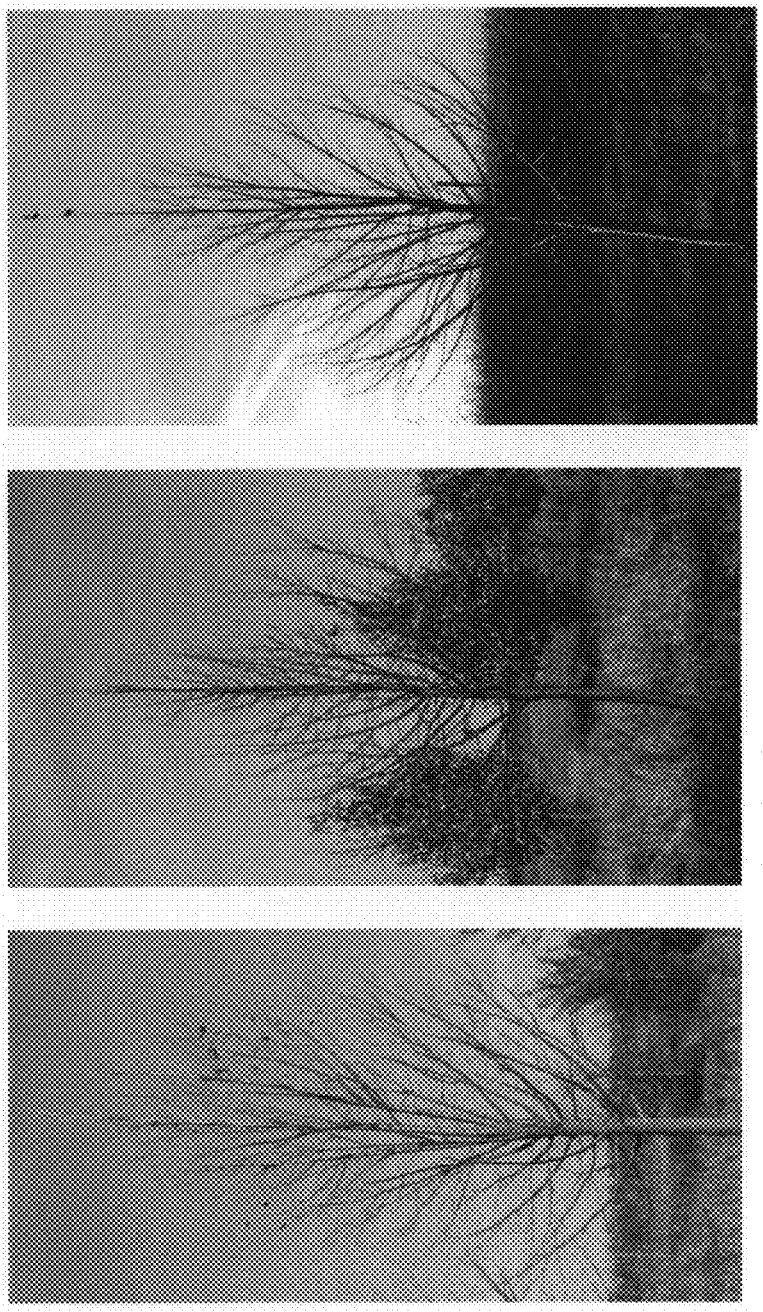
FIG. 4 illustrates a comparison of trees of 'Kromm', appearing on the left, 'Redmond', in the center and 'McKSentry' on the right.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'KROMM' plants grown outdoors and in a nursery in Jackson, Wis. Plants were initially measured during late Autumn. Age of the plants when described is approximately 16 years old. Measurements and numerical values represent averages of typical plant types.

Botanical classification: *Tilia americana* 'KROMM'.

PROPAGATION

Trees are typically chip bud grafted. A 5 to 6 foot whip will result from a chip bud in approximately 2 years in Southern Wisconsin.

Root description: Woody. Brown roots not accurately measured with an R.H.S. chart.

PLANT

Growth habit: Pyramidal tree, somewhat narrow. Dense crown.

Height: 24 feet.

Spread: 10 feet.

Growth rate: 12 to 18 inches of terminal growth per year on a 15 year old plant. 4 to 8 inches of growth per year on lowest ⅓ lateral branches. 6 to 12 inches of growth per year on center ⅓ lateral branches.

Branch internode length: About 4.5 cm, reducing to 3 cm towards upper crown.

Branch characteristics:

- *Length*.—Main branches are 3 to 7 feet long, sub-lateral average length range about 10 to 30 inches.
- *Diameter*.—Main branches about 1.5 to 1.75 inches. Sub-lateral diameter about 0.5 inch.
- *Texture*.—Smooth with non-scaly striations.
- *Color*.—Near RHS Grey 201C.

Aspect and angle: Lowest branches occur at about 85° angle from trunk. Middle branches occur at about 45° angle from trunk. Upper branches occur at about 15 to 20° angle from trunk.

Trunk characteristics:

- *Diameter*.—About 7 inches measured at approximately 5 inches above soil level at 15 years.
- *Color*.—Near RHS Grey 201B.
- *Bark texture*.—Striated ridges. On average 8 to 18 mm wide and about 10 to 20 mm deep.

Other branch and trunk characteristics:

- *Branch buds*.—2, or sometimes 3 scales present. Bud shape: broad conical, about 5 to 8 cm long, 4 to 6 cm wide. Coloration (Mid-November): Near Red-Purple 59B, margin 59A, very immature margin near Green 143A.
- *Lenticels present*.—Yes. Inconspicuous.
- *Lenticel length*.—Less than 1.0 mm.
- *Lenticel diameter*.—Less than 0.5 mm.
- *Lenticel density*.—Moderate.
- *Lenticel color*.—Near RHS Brown N200B.

FOLIAGE

Leaf:

- *Arrangement*.—Alternate.
- *Average length*.—Approximately 10 to 11 cm excluding petiole.
- *Average width*.—Approximately 8.3 to 9.2 cm.
- *Shape of blade*.—Asymmetrical broad deltate.
- *Apex*.—Acuminate. Acuminate tip 1.0 to 1.5 cm.
- *Base*.—Asymmetrical truncate.
- *Margin*.—Serrate to double serrate. Serration highly acute but not sharp.
- *Texture of top surface*.—Glabrous.
- *Texture of lower surface*.—Glabrous.
- *Color*.—Young foliage: Upper side: Near RHS Yellow-Green 144A. Under side: Near RHS Yellow-Green 144B. Mature foliage: Upper side: Near RHS Green 137A. Under side: Near RHS Green 137C. Mature Fall foliage (October in Wisconsin): Upper side: Near RHS Yellow-Green 147A. Under side: Near RHS Yellow-Green 146A.

Foliage:

- *Venation*.—Type: Pinnate. Color: Venation color upper side: Near RHS Yellow-Green N144B. Venation color under side: Near RHS Yellow-Green N144B.
- *Petiole*.—Length: Average 5.5 cm. Diameter: Average 0.2 cm. Color: Upper side: Near RHS Yellow-Green 145B. Under side: Near RHS Yellow-Green 145B.

FLOWER

Flowering begins: Around Mid June to early July in Wisconsin.

Inflorescence: Compound umbel. Approximately 5 cm in diameter and 4 cm deep. Average 11 flowers per inflorescence. Hanging aspect. The inflorescence emerges from a petiolate bract.

Inflorescence bract:

- *Average length*.—Approximately 7 to 11 cm.
- *Average width*.—Approximately 11 to 16 mm.
- *Shape of blade*.—Oblong.
- *Apex*.—Acute.
- *Base*.—Truncate.
- *Margin*.—Entire.
- *Texture of top surface*.—Glabrous.
- *Texture of lower surface*.—Glabrous.

*Color*.—Upper side: Near RHS Yellow-Green 144A. Under side: Near RHS Yellow-Green 145A. Fall color near Grey-Brown 199B, upper and lower surfaces.

*Inflorescence bract petiole*.—Length: Unattached average 5 mm, 4 cm further until petiole begins. Diameter: Average 2 mm. Color: Upper side: Near RHS Yellow-Green 151D. Under side: Near RHS Yellow-Green 151C.

Individual flower size:

*Diameter*.—9 to 11 mm.

*Length*.—7 mm.

Petals:

*Length*.—6 mm.

*Width*.—3 mm.

*Quantity*.—5.

*Texture*.—Glabrous.

*Apex*.—Acute.

*Base*.—Truncate.

*Margin*.—Entire.

Color:

*Upper surface*.—Near Yellow-White 158C.

*Lower surface*.—Near Yellow-White 158C.

Calyx/sepals:

*Quantity per flower*.—5.

*Shape*.—Narrow deltate, strongly convex.

*Length*.—6 mm.

*Width*.—3 mm.

*Apex*.—Acute.

*Base*.—Truncate.

*Margin*.—Entire.

*Texture*.—Glabrous.

*Color*.—Upper Surface: Near Yellow-Green 151C. Lower Surface: Near Yellow-Green 151B.

Peduncle:

*Length*.—Average 5.5 cm.

*Diameter*.—1-2 mm.

*Color*.—Near Yellow-Green N144B.

*Texture*.—Glabrous.

*Strength*.—Flexible and moderately strong.

Pedicel:

*Length*.—8 to 25 mm.

*Diameter*.—1 mm.

*Color*.—Near Yellow-Green 144B.

*Texture*.—Glabrous.

*Strength*.—Flexible and moderately strong.

REPRODUCTIVE ORGANS

Gynoecium:

Pistil:

*Number*.—1.

*Length*.—9 mm.

*Style*.—Length: 5 mm. Color: Near Yellow-Green 154D.

*Stigma*.—Shape: Linear. Color: Near Greyed-Orange 178A.

*Ovary*.—Ovary shape: Spherical. Ovary size: 5 mm diameter. Ovary Color: Near Yellow-Green 150B.

Androecium:

Stamens:

*Number*.—5 to 7 clusters of 5.

*Filament length*.—2 to 4 mm.

Anthers:

*Length*.—Less than 1 mm.

*Shape*.—Linear.

*Color*.—Near Greyed-Red 178B.

*Pollen*.—Scant or none. Colored near Greyed Yellow 161D.

OTHER CHARACTERISTICS

Fruits: Dry nutlets. Spherical, about 8 to 9 mm in diameter. Very short, soft pubescent, velvety. Colored near Grey-Brown 199B.

Disease resistance: Tolerant to normal diseases.

Pest resistance: Tolerant to normal pests. Increased resistance to Japanese beetle.

Drought resistance: Resists late season leaf scorch in Wisconsin which is typically associated with dry conditions.

Temperature tolerance: Tolerant to high temperatures, to 100° F. and low temperatures to at least: −25° F.

What is claimed is:

1. A new and distinct cultivar of *Tilia americana* tree named 'KROMM' as herein illustrated and described.

* * * * *

'Kromm' 'Redmond' 'McSentry'